(12) United States Patent
Lee et al.

(10) Patent No.: US 7,626,115 B2
(45) Date of Patent: Dec. 1, 2009

(54) DYE HAVING DISPERSANT FUNCTION AND SOLAR CELL COMPRISING THE SAME

(75) Inventors: Eun Sung Lee, Seoul (KR); Won Cheol Jung, Seoul (KR); Sang Cheol Park, Seoul (KR); Young Jun Park, Gyeonggi-do (KR); Jung Gyu Nam, Gyeonggi-do (KR); Jin Young Bae, Seoul (KR)

(73) Assignee: Samsung Electronics Co., Ltd. (KR)

( * ) Notice: Subject to any disclaimer, the term of this patent is extended or adjusted under 35 U.S.C. 154(b) by 267 days.

(21) Appl. No.: 11/560,606

(22) Filed: Nov. 16, 2006

(65) Prior Publication Data

US 2007/0277871 A1 Dec. 6, 2007

(30) Foreign Application Priority Data

Jan. 1, 2006 (KR) ............... 10-2006-0049287

(51) Int. Cl.
*H01L 31/0256* (2006.01)
*C07F 15/00* (2006.01)
(52) U.S. Cl. ............... 136/252; 257/E51.02; 546/2
(58) Field of Classification Search ............... 136/252; 546/2; 257/E51.02
See application file for complete search history.

(56) References Cited

U.S. PATENT DOCUMENTS 5,350,644 A * 9/1994 Graetzel et al. ............. 429/111

FOREIGN PATENT DOCUMENTS

| JP | 2002050413 | 2/2002 |
| KR | 1020050082624 A | 8/2005 |

* cited by examiner

*Primary Examiner*—Rebecca L Anderson
*Assistant Examiner*—Joseph R Kosack
(74) *Attorney, Agent, or Firm*—Cantor Colburn LLP (57) ABSTRACT

Disclosed are a novel dye, having a dispersant functional group to simultaneously exhibit a dye function and a dispersant function, and a dye-sensitized solar cell including the same. According to this invention, the dye may simultaneously manifest a dye function for absorbing light, made possible by being adsorbed on the entire surface of metal oxide particles, to thus produce excited electrons which are then transferred into a conduction band of metal oxide, and a dispersant function for preventing the agglomeration of the particles to thus improve the uniformity of the metal oxide particles in a paste and film density.

6 Claims, 2 Drawing Sheets

DYE HAVING DISPERSANT FUNCTION AND SOLAR CELL COMPRISING THE SAME

This non-provisional application claims priority under U.S.C. § 119(a) from Korean Patent Application No. 2006-49287 filed on Jun. 1, 2006, the entire contents of which are hereby incorporated by reference.

BACKGROUND OF THE INVENTION

1. Field of the Invention

The present invention relates, generally, to a dye that can function as a dispersant and a solar cell comprising the dye. In one embodiment, the dye comprises a dispersant functional group so as to simultaneously exhibit a dye function and a dispersant function.

2. Description of the Related Art

A dye-sensitized solar cell is a photoelectrochemical solar cell composed mainly of a photosensitive dye molecule for absorbing visible light to produce electron-hole pairs, and transition metal oxide for transferring the produced electrons.

Such a dye-sensitized solar cell consists of a semiconductor electrode, an electrolyte, and a counter electrode, in which the semiconductor electrode includes a conductive transparent substrate and a light absorbing layer including a metal oxide and a dye.

The semiconductor electrode is obtained by forming a metal oxide film on a substrate and then adsorbing a dye on the film. Specifically, a paste composition of metal oxide is applied on a transparent substrate and then burned at a high temperature of about 400 to about 550° C. to form a metal oxide film, which is then immersed in a dye-dissolved solution for a predetermined period of time to adsorb the dye on the surface of the film.

In this way, in the formation of the semiconductor electrode of a dye-sensitized solar cell, since the metal oxide film is formed on the substrate and then the dye is adsorbed on the film, it is difficult to use the entire surface area of the metal oxide particles, thus causing a problem in which the adsorbed amount of dye is very small relative to the optical cross-section of light. When the amount of dye adsorbed is small, the photoelectric efficiency of the solar cell is decreased.

Further, in the case where the metal oxide film is formed using nanoparticles, agglomeration of the nanoparticles in the paste may occur, thereby undesirably reducing the uniformity and density of the metal oxide film, leading to decreased photoelectric efficiency of the solar cell.

In this regard, Korean Patent Laid-open Publication No. 2005-82624 discloses a dye-sensitized solar cell manufactured by forming a porous film of metal oxide through an electrochemical process using a surfactant and then adsorbing a dye thereon, so as to increase the photoelectric efficiency of the solar cell. In addition, Japanese Patent Laid-open Publication No. 2002-50413 discloses a dye-sensitized solar cell, which comprises a photosemiconductor layer composed of porous photosemiconductor particles obtained by burning photosemiconductor powder in the presence of a surfactant or a hydrophilic polymer compound and a dispersion medium at a temperature of 400° C. or higher and then milling it.

According to such conventional techniques, in which the surfactant or dispersant is to the metal oxide film, the porous properties of the metal oxide or photosemiconductor particles are enhanced by the introduction of the surfactant, therefore slightly increasing the adsorbed amount of dye and the uniformity of the metal oxide film. However, since the dye adsorption process is usually performed after the formation of the metal oxide film or semiconductor layer, it is difficult to use the entire surface area of the metal oxide particles, and consequently it is impossible to sufficiently increase the adsorbed amount of dye and the photoelectric efficiency.

SUMMARY OF THE INVENTION

Accordingly, the present invention is directed to providing a novel dye for increasing dispersibility and uniformity of a paste composition while exhibiting good adsorptivity to metal oxide particles.

The present invention also provides a semiconductor electrode having uniform properties and superior processibility.

The present invention also provides a solar cell comprising the semiconductor electrode, thus exhibiting high photoelectric efficiency.

The present invention further provides a dye, which has a dispersant functional group so as to simultaneously behave as a dye as well as a dispersant.

In addition, the present invention provides a paste composition, comprising the above dye, a low-temperature burning binder solution, and metal oxide powder.

In addition, the present invention provides a semiconductor electrode, comprising a transparent electrode including a substrate and a conductive material applied thereon, a metal oxide layer formed on the transparent electrode, and the above dye.

In addition, the present invention provides a method of manufacturing a semiconductor electrode, applying the above paste composition on a transparent substrate coated with conductive material, and burning the applied composition at about 80 to about 200° C. for about 0.5 to about 5 hours, thus forming a light absorbing layer.

In addition, the present invention provides a dye-sensitized solar cell, comprising the above semiconductor electrode, an electrolyte layer, and a counter electrode.

DESCRIPTION OF THE PREFERRED EMBODIMENTS

Hereinafter, a detailed description will be given of the present invention.

According to the present invention, the novel dye has a hydrophilic and hydrophobic block type dispersant tail structure, and specifically comprises a dye ligand having a reactive group, such as $COO^-$, $NH_3^+R^-$, or the like. The reactive group can be used for reacting the novel dye with the surface of metal oxide particles. The dispersant tail functions as a stabilizer for preventing the agglomeration of the particles in a paste composition.

Particularly, the dye of the present invention is represented by Formula 1 below:

Formula 1 wherein $R_a$, $R_b$, $R_c$ and $R_d$ are each independently $H^+$ or are represented by Formula 2 below. As such, at least one of $R_a$, $R_b$, $R_c$ and $R_d$ is represented by Formula 2 below:

Formula 2 wherein $X_1$, $X_2$, $X_3$ and $X_4$ are each independently H or a methyl group, A is a substituted or unsubstituted $C_{6-30}$ arylene group, a substituted or unsubstituted $C_{6-30}$ arylalkylene group, or a substituted or unsubstituted $C_{6-30}$ cycloalkylene group, B is a substituted or unsubstituted $C_{1-20}$ alkyl group, a substituted or unsubstituted $C_{1-20}$ alkenyl group, or a substituted or unsubstituted $C_{1-20}$ alkynyl group, which may be present in a linear or branched type, m is an integer from 1 to 20, and n is 0 or 1.

Therefore, the dye in addition to its dispersant capabilities may simultaneously exhibit a dye function for absorbing light. Upon being disposed upon the surface of the metal oxide particles, the dye absorbs light and produces excited electrons, which are then transferred into to a conduction band in the metal oxide. The dispersant function prevents agglomeration of the particles to improve the uniformity of distribution of the metal oxide particles in the paste and the film density. Therefore, the semiconductor electrode and solar cell, manufactured using the paste composition comprising the dye display both improved photoelectric efficiency and processability.

In one embodiment, the dispersant tail of the dye, which is represented by Formula 2, comprises four moieties of $NH_3^+$-polyethyleneglycol (PEG)-ring compound-alkyl.

Of these moieties, the ring compound moiety (A in Formula 2) may be a substituted or unsubstituted $C_{6-30}$ arylene group, a substituted or unsubstituted $C_{6-30}$ arylalkylene group, or a substituted or unsubstituted $C_{6-30}$ cycloalkylene group, and the alkyl moiety (B in Formula 2) is a substituted or unsubstituted $C_{1-20}$ alkyl group, a substituted or unsubstituted $C_{1-20}$ alkenyl group, or a substituted or unsubstituted $C_{1-20}$ alkynyl group, which may be present in a linear or branched type.

Specific examples of the alkyl group include linear or branched methyl, ethyl, propyl, isobutyl, sec-butyl, tert-butyl, pentyl, iso-amyl, and hexyl, at least one hydrogen atom of the alkyl group being substituted with a halogen atom, a hydroxyl group, a nitro group, a cyano group, an amino group, an amidino group, hydrazine, or hydrazone.

The alkenyl or alkynyl group denotes a radical containing a carbon double bond or triple bond at the middle site or end site of the alkyl group defined above, at least one hydrogen atom of the alkenyl or alkynyl group being substituted with the same substituent as in the alkyl group.

The arylene group denotes a carbocyclic aromatic system containing one or more aromatic rings, the rings being attached or fused together. Specific examples of the arylene group include aromatic groups, such as phenyl, naphthyl, tetrahydronaphthyl, or the like, at least one hydrogen atom of the arylene group being substituted with the same substituent as in the alkyl group.

The arylalkylene group denotes a radical in which some of the hydrogen atoms of the arylene group defined above are substituted with lower alkylene, such as, for example, methylene, ethylene, propylene, benzylene and phenylethylene, at least one hydrogen atom of the arylalkylene group being substituted with the same substituent as in the alkyl group.

The cycloalkylene group denotes a $C_6$ to about $C_{30}$ monovalent monocyclic system, at least one hydrogen atom of the cycloalkylene group being substituted with the same substituent as in the alkyl group.

In the dispersant tail of the dye as shown in the Formula 2, the number of PEG moieties is about 5 to about 10 and the number of alkyl moieties that are preferably present in a branched arrangement is 5 or more. This is because the power of adsorption to the surface of the particles is enhanced as the length of PEG decreases. As well, when the alkyl moiety is lengthened and is more bulky, predetermined intervals between the particles are maintained, thus further increasing stability.

Specifically, examples of the dye of the present invention include, but are not limited to, compounds represented by Formulas 3 to 6 below:

Formula 3

Formula 4

Formula 5

Formula 6 wherein X is $R_1$, $R_2$, $R_3$, $R_4$ and $R_5$ are each independently H or a methyl group, and m is an integer from about 5 to about 10, l is 0 or 1, and k is an integer from about 2 to about 10.

More specifically, examples of the dye of the present invention include a compound represented by Formula 7 below:

Formula 7

The dye of the present invention, represented by Formula 1, may be synthesized using a typical synthesis process known in the art without limit, and preferably may be synthesized according to the reaction path of Reaction 1 below:

adding the dye solution with a dispersant of Formula 8 below to cause the mixture to react for a predetermined period of time, removing the organic solvent, and filtering and purifying the resultant product:

Reaction 1 wherein in Reaction 1, $X_1$, $X_2$, $X_3$, $X_4$, A, B, m and n are as defined in Formula 2.

Particularly, the dye of the present invention is synthesized as follows.

That is, the dye of the present invention is synthesized by dissolving a dye in an organic solvent to form a dye solution, Formula 8

$$NH_2-\left(\begin{matrix}X_1\\|\\C\\|\\X_2\end{matrix}-\begin{matrix}X_3\\|\\C\\|\\X_4\end{matrix}-O\right)_m-A_n-B$$

wherein $X_1$, $X_2$, $X_3$, $X_4$, A, B, m and n are as defined in Formula 2.

In the above reaction, examples of useful dyes include dichloromethane ($CH_2Cl_2$), triethylamine, toluene, dimethoxyether, tetrahydrofuran, or dimethylformamide. In addition, specific examples of the dye include Ruthenium 535 ($N_3$ dye), but any dye may be used without limit as long as it is typically used in the field of solar cells. Preferably, a Gratzel dye, such as a ruthenium complex, including $N_3$, $N_{719}$, or Black Dye, is used.

Further, the above reaction preferably proceeds at a temperature ranging from room temperature to 80° C. for about 2 to about 24 hours in a nitrogen atmosphere, and the filtration, drying and purification processes may be performed using typical processes known in the related art without limit.

In addition, the present invention provides a paste composition comprising the above-mentioned dye for formation of a semiconductor electrode.

Specifically, the paste composition of the present invention comprises the dye, a low-temperature burning binder solution, and metal oxide powder.

In the conventional dye-sensitized solar cell, the semiconductor electrode is formed in a manner such that a metal oxide film is formed on a substrate and then a dye is adsorbed on the film. Thus, since the entire surface area of the metal oxide particles is not used, the adsorbed amount of dye is equal to merely 1/10 of the optical cross-section of light.

On the other hand, in the present invention, when preparing the paste composition for the formation of the semiconductor electrode, the above dye having a dispersant function is added in a slurry dispersion step, thereby simultaneously increasing the adsorbed amount of dye over the entire surface of the metal oxide particles and improving the dispersibility and uniformity of the metal oxide particles. As a result, the semiconductor electrode and solar cell, manufactured using the paste composition of the present invention, can exhibit improved processibility and photoelectric efficiency.

In the paste composition of the present invention, a low-temperature burning binder, which may be easily removed through a low-temperature burning process, is used. Specific examples of the low-temperature burning binder include t-butanol. Said t-butanol has a melting point of 25 to 26° C. and a boiling point of 80° C. Hence, t-butanol may be exclusively removed through a low-temperature burning process of about 350° C. or less, and is present in a solid state at 25° C. or less, and thus imparts a strong binding effect due to a hydrogen bonding when dried.

Consequently, unlike a conventional paste composition, which is difficult to apply to a flexible plastic substrate using a binder which is removable only through a high-temperature heat treatment of 350° C. or higher, the paste composition of the present invention is advantageously applied to flexible substrates, such as plastics, without limit, thanks to the use of a binder having the above properties, such as t-butanol.

The paste composition of the present invention comprises about 20 to about 50 wt % of metal oxide powder, and about 0.1 to about 10 wt % of the dye based on the powder, with the balance being the binder solution.

In the case where the dye of the present invention is used in an amount less than about 0.1 wt % based on the metal oxide powder, it is impossible to increase the adsorbed amount of dye and to inject excited electrons into the conduction band of metal oxide. The dispersant effect may also not be realized. On the other hand, if the amount of dye exceeds about 10 wt %, excess dye which is not adsorbed on $TiO_2$ causes an electrochemical side-reaction, undesirably decreasing efficiency.

Further, the low-temperature burning binder solution is preferably a mixture solution comprising a solvent and t-butanol mixed at a ratio of about 1:1 to about 1:10 (w/w) As such, if t-butanol is added to the solvent in a ratio of less than 1:1 (w/w), the amount of solvent is larger than the amount of the t-butanol binder, thus the viscosity of the paste is decreased, undesirably weakening adhesion. Consequently, the resulting semiconductor electrode has poor quality. On the other hand, if t-butanol is added in a ratio greater than 1:10 (w/w), the initial viscosity is increased leading to a decrease of loading of $TiO_2$. Ultimately, this leads to semiconductor electrodes not having good quality and desired properties.

As such, the solvent for the binder solution can comprise organic solvent or water without limit. Preferably, useful is a solvent that is more polar than t-butanol and has a high hydrogen bond index. Such a solvent is exemplified by water, glycol, and glycerin. More preferably, an aqueous solvent may be used.

Moreover, when a great number of OH groups is present in the paste composition, the composition has increased viscosity, and is thus difficult to apply. In order to prevent such a phenomenon, an acetate-based solvent, including ethyl acetate, butyl acetate, propylene glycol methyl ether acetate, propylene glycol monoether acetate (PGMEA), or DHTA, may be further added.

The metal oxide powder used in the paste composition of the present invention comprises at least one selected from the group consisting of titanium oxide, niobium oxide, hafnium oxide, indium oxide, tin oxide and zinc oxide, which may be used alone or in combinations thereof. In particular, titanium oxide ($TiO_2$) is preferable.

It is generally desirable for the metal oxide to be in nano-particle form such as, for example, quantum dots, nano-dots, nanotubes, nanowires, nanobelts, or nanoparticles. The particle size of metal oxide preferably ranges from about 5 to about 400 (nanometers) nm.

In addition, the present invention provides a semiconductor electrode, manufactured using the above-mentioned paste composition.

Specifically, the semiconductor electrode of the present invention comprises a transparent electrode including a substrate and a conductive material applied thereon, a metal oxide layer formed on the transparent electrode, and the dye of Formula 1 present in the metal oxide layer.

As such, the substrate constituting the transparent electrode may be used without limit so long as it is transparent, and specific examples thereof include a glass substrate, a silica substrate, and a plastic substrate.

Examples of the conductive material, which is applied on the substrate, include indium tin oxide (ITO), fluorine-doped tin oxide (FTO), $ZnO$—$Ga_2O_3$, $ZnO$—$Al_2O_3$, $SnO_2$—$Sb_2O_3$, or the like, or a combination comprising at least one of the foregoing metal oxides.

Examples of suitable polymers that may be used in plastic substrates are polycarbonate, polymethylmethacrylate, polyetherimide, polyester, polystyrene, or the like, or a combination comprising at least one of the foregoing polymers.

In the present invention, the method of manufacturing the semiconductor electrode comprises applying the paste composition of the present invention on a transparent substrate coated with a conductive material and burning the applied paste composition at about 80 to about 200° C. for about 0.5 to about 5 hours, thus forming a light absorbing layer.

Since the semiconductor electrode manufacturing method according to the present invention is performed using the paste composition including both the dye of the present invention and metal oxide, it does not require conventional processes of forming a metal oxide film and then adsorbing a dye thereon. Moreover, due to the use of t-butanol having a boiling point of 80° C. as the binder, the light absorbing layer can be formed even by the low-temperature burning process at about 80 to about 200° C., resulting in economical manufacturing costs and processes.

In addition, the use of a low temperature burning process makes the process amenable to use on plastic substrates as well.

The paste composition may be applied, for example, by spraying, spin coating, dipping, printing, doctor blading or sputtering, a chemical deposition process, a physical deposition process, or an electrophoresis process. The applied composition is dried through a typical process and then low-temperature burned at about 80 to about 200° C. for about 0.5 to about 5 hours, thus forming a light absorbing layer. As such, the burning process may be conducted at about 90 to about 150° C. for about 1 to about 3 hours.

The light absorbing layer may have a planar surface structure or an uneven surface structure to increase the surface area thereof so as to increase the degree of adsorption to the electrolyte layer. Examples of the uneven structure include, but are not limited to, a stepped shape, a needle shape, a mesh shape, and a scar shape.

Although the light absorbing layer may be formed as a monolayer, it may be formed into a double layer using two paste compositions including two types of metal oxides each having different particle sizes, thereby increasing light transmittance. Preferably, the first paste composition including metal oxide having a particle size of 9~20 nm is applied to a thickness of about 10 to about 20 micrometers (μm), and the second paste composition including metal oxide having a particle size of about 200 to about 400 nm is applied to a thickness of about 3 to about 5 μm, thus realizing the double layer.

The semiconductor electrode of the present invention has superior processability, high adsorptivity of the dye to metal oxide, and uniform film properties. Thus, in the case where it is applied to a dye-sensitized solar cell, photoelectric efficiency may be increased.

The dye-sensitized solar cell, which is provided with the semiconductor electrode of the present invention, comprises a semiconductor electrode, an electrolyte layer, and a counter electrode.

The electrolyte layer is formed with an electrolyte solution, for example, a solution of iodine in acetonitrile, NMP or 3-methoxypropionitrile, but the present invention is not limited thereto. Further, any electrolyte may be used without limit, as long as it has a hole transport function.

The counter electrode can be formed using any conductive material without limit, and may also be made of an insulating material having a conductive layer that faces the semiconductor electrode. As such, the electrode must be formed of electrochemically stable material, in particular, platinum, gold, and carbon, or carbon nanotubes.

A thin layer of conductive polymers such as polypyrrole, polyaniline, polythiophene, polyacetylene may also be used to form the counter electrode.

Furthermore, the surface of the counter electrode that faces the semiconductor electrode preferably has a fine structure, and therefore an enlarged surface area. For instance, it is preferred that platinum be in a state of platinum black and that carbon be in a state of porous carbon. The platinum black state may be formed through a platinum anodization process or chloroplatinic acid treatment, and the porous carbon state may be formed through a process of sintering carbon particles or a process of burning organic polymer.

The method of manufacturing the dye-sensitized solar cell having the above structure is not particularly limited, and any method known in the related art may be used without limit.

A better understanding of the present invention may be obtained in light of the following synthesis examples and examples, which are set forth to illustrate, but are not to be construed to limit the present invention.

SYNTHESIS EXAMPLE

Synthesis of Dye of the Present Invention

-continued (1) Synthesis of Triton X-100-Mesylate 10 g (16 mmol) of Triton®X-100, available from Aldrich, was dissolved in anhydrous methylene chloride (20 ml). The solution was added with 4.86 g (48 mmol) of triethylamine, available from Aldrich, and then stirred in a nitrogen atmosphere for 10 min.

The reactor was placed into an ice bath, after which the reaction was conducted for 1 hour while 5.5 g (48 mmol) of methanesulfonyl chloride, available from Aldrich, was added slowly. Subsequently, the temperature was gradually increased to room temperature, while the reactants were stirred for 3 hours.

After the completion of the reaction, the reaction product was poured on ice water to separate an organic layer, which was then washed with a brine solution. The methylene chloride solution thus obtained was evaporated using a rotary evaporator to remove the solvent, and then the obtained viscous liquid was dried in a vacuum oven, yielding Triton X-100-mesylate.

(2) Synthesis of Triton X-100-Amine 10.2 g (14.52 mmol) of the Triton X-100-mesylate obtained in (1) was dissolved in 20 ml of ethanol and stirred at room temperature for 15 min. This solution was added with 11.16 g (217.8 mmol) of an ammonia solution (2.0 M dissolved in ethanol), available from Aldrich, and refluxed for 12 hours while being stirred.

After the completion of the reaction, the reaction product was poured on excess ice water, and then an organic layer was extracted using methylene chloride and then washed with a brine solution.

The methylene chloride solution thus obtained was evaporated using a rotary evaporator to remove the solvent, and then the obtained viscous liquid was dried in a vacuum oven, yielding Triton X-100-amine.

(3) Synthesis of Ruthenium Dye Having Triton X-100-Amine 70 mg (0.094 mmol) of Ruthenium 535 ($N_3$ dye), available from Solaronix, and 234.2 mg (0.376 mmol) of TX-100-amine were dissolved in 10 ml of ethanol, and then stirred at room temperature for 1 hour.

The reaction solution was evaporated using a rotary evaporator to remove the solvent. In the resulting viscous liquid, a small amount of methylene chloride was dissolved, and the solution thus obtained was poured on n-hexane to form a precipitate. Thereafter, a drying process was conducted in a vacuum oven, thereby obtaining a ruthenium dye containing Triton X-100-amine.

PREPARATIVE EXAMPLE

Preparation of Paste Composition 7 g of a binder solution comprising water and t-butanol mixed at a ratio of 1:2 (w/w) was mixed with 120 mg of the dye obtained in the synthesis example and then stirred for 30 min. To the solution thus mixed was added with 3 g of $TiO_2$ powder having a particle size of 13 nm and stirred for 1 hour, thus obtaining the paste composition of the present invention.

EXAMPLE 1

Manufacture of Conductor Electrode and Solar Cell (1)

(1) Manufacture of Semiconductor Electrode

On a plastic substrate, fluorine-doped tin oxide (FTO) was applied by sputtering. Then, the paste composition obtained in the preparative example was applied using a screen printing process and burned at 120° C. for 1 hour, thus forming a light absorbing layer about 20 μm thick, thereby completing the semiconductor electrode of the present invention.

(2) Manufacture of Solar Cell

On the surface of a conductive transparent plastic substrate coated with ITO, platinum was applied, thus forming a counter electrode. Subsequently, the counter electrode, acting as an anode, and the semiconductor electrode obtained in (1), acting as a cathode, were assembled. When the two electrodes were assembled, the conductive surfaces of the anode and the cathode were disposed to face each other in the cell. This arrangement permitted the platinum layer and the light absorbing layer to face each other. In addition, a polymer layer about 40 μm thick formed of SURLYN® (available from Du Pont) was provided between the anode and the cathode, after which the two electrodes were compressed at about 1 to about 3 atmospheres on a heating plate at about 100 to about 140° C. The polymer layer was attached to the surfaces of the two electrodes by heat and pressure.

Thereafter, the space between the two electrodes was filled with an electrolyte solution via fine holes formed in the surface of the anode, consequently completing the dye-sensitized solar cell of the present invention. As the electrolyte solution, an $I^{3-}/I^-$ electrolyte solution, prepared by dissolving 0.6 M 1,2-dimethyl-3-octyl-imidazolium iodide, 0.2 M LiI, 0.04 M $I_2$ and 0.2 M 4-tert-butyl pyridine (TBP) in acetonitrile, was used.

EXAMPLE 2

Manufacture of Conductor Electrode and Solar Cell (2)

A dye-sensitized solar cell was manufactured in the same manner as in Example 1, with the exception that a layer of $TiO_2$ 17.720 μm thick was used as the metal oxide layer.

COMPARATIVE EXAMPLE 1

Manufacture of Conductor Electrode and Solar Cell

A dye-sensitized solar cell was manufactured in the same manner as in Example 1, with the exception that Ruthenium 535 ($N_3$ dye) was used as the dye and a layer of $TiO_2$ 16.600 μm thick was used as the metal oxide layer.

COMPARATIVE EXAMPLE 2

Manufacture of Conductor Electrode and Solar Cell

A dye-sensitized solar cell was manufactured in the same manner as in Comparative Example 1, with the exception that a layer of $TiO_2$ 17.288 μm thick was used as the metal oxide layer.

COMPARATIVE EXAMPLE 3

Manufacture of Conductor Electrode and Solar Cell

A dye-sensitized solar cell was manufactured in the same manner as in Example 1, with the exception that N719 was used as the dye and a layer of $TiO_2$ 16.559 μm thick was used as the metal oxide layer.

COMPARATIVE EXAMPLE 4

Manufacture of Conductor Electrode and Solar Cell

A dye-sensitized solar cell was manufactured in the same manner as in Comparative Example 3, with the exception that a layer of $TiO_2$ 17.258 μm thick was used as the metal oxide layer.

TEST EXAMPLE

Evaluation of Photoelectric Efficiency of Solar Cell

The photovoltage and photocurrent of each of the solar cells of Examples 1 and 2 and Comparative Examples 1 to 4 were measured, and thus photoelectric efficiency was calculated. As such, a light source (Xenon lamp, Oriel, 01193) was used, the radiation condition (AM 1.5) of the Xenon lamp being corrected using a standard solar cell (Fraunhofer Institute Solare Engeriessysteme, Certificate No. C-ISE369, Type of material: Mono-$Si^+$ KG filter).

The photocurrent density ($J_{sc}$), open-circuit voltage ($V_{oc}$) and fill factor (FF), calculated from the measured photocurrent-voltage curve, were substituted into Equation 1 below, thus calculating the photoelectric efficiency ($\eta_e$). The results are given in Table 1 below, along with the thickness of the layer of $TiO_2$ used in the dye-sensitized solar cell.

$$\eta_e = (V_{oc} \cdot J_{sc} \cdot FF)/(P_{inc}) \qquad \text{Equation 1}$$

wherein $P_{inc}$ shows 100 mW/cm² (1 sun)

TABLE 1

| No. | $J_{sc}$ (mA/cm²) | $V_{oc}$ (mV) | FF | $\eta_e$ (%) | $TiO_2$ Layer((m) |
|---|---|---|---|---|---|
| Ex. 1 | 10.572 | 640.922 | 0.738 | 5.023 | 16.739 |
| Ex. 2 | 10.546 | 620.904 | 0.713 | 4.688 | 17.720 |
| C. Ex. 1 | 8.773 | 589.706 | 0.699 | 3.631 | 16.600 |
| C. Ex. 2 | 9.787 | 603.938 | 0.745 | 4.421 | 17.288 |
| C. Ex. 3 | 9.333 | 637.220 | 0.762 | 4.548 | 16.559 |
| C. Ex. 4 | 9.212 | 596.140 | 0.700 | 3.861 | 17.258 |

As is apparent from Table 1, it has been confirmed that the solar cell of the present invention has increased photoelectric efficiency, due to the introduction of a triton-based dispersant, having good affinity to TiO2, to a conventional ruthenium dye.

Figure 1:
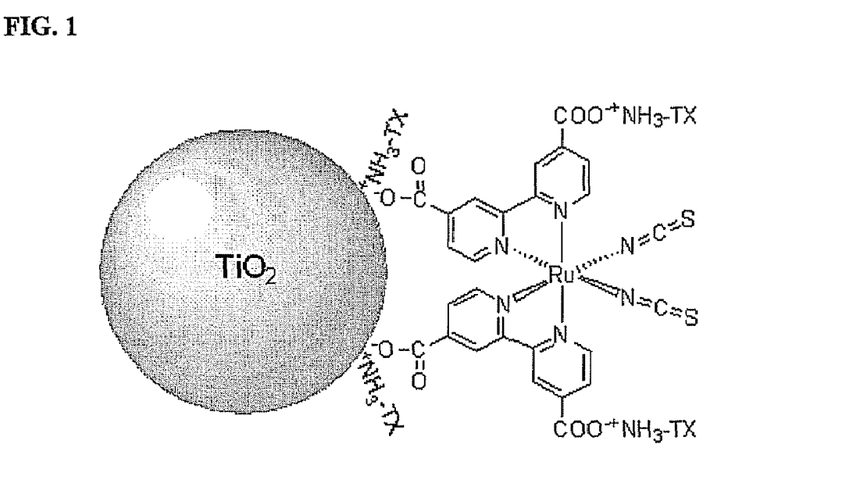
FIG. 1 is an exemplary schematic view showing the dye adsorbed on the surface of $TiO_2$, according to the present invention.
Figure 2:
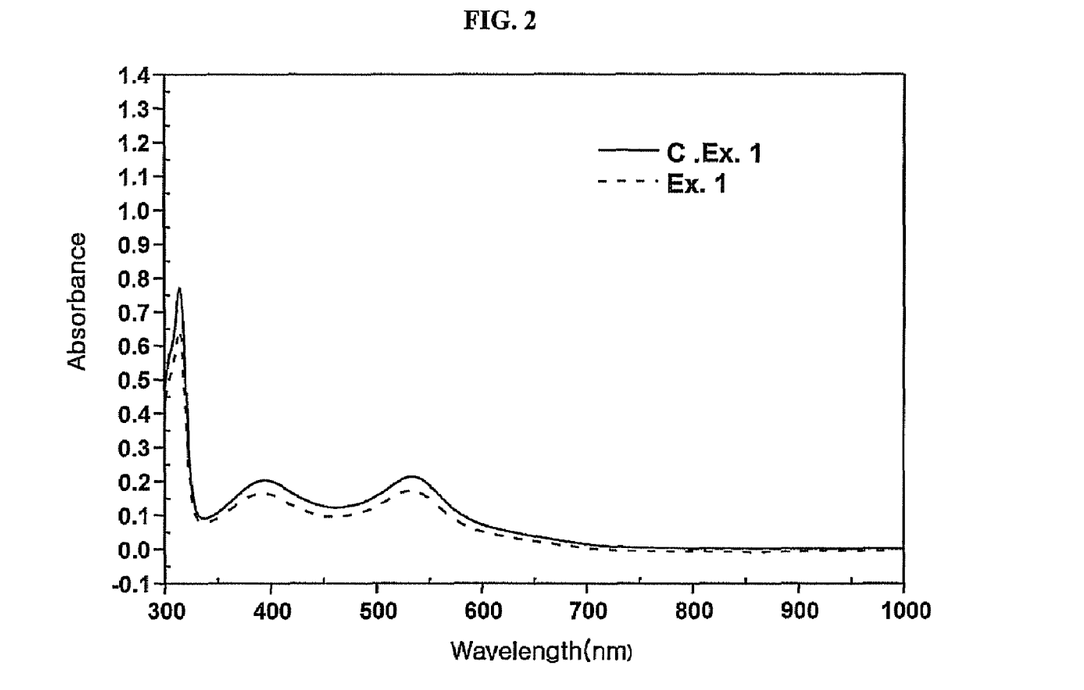
FIG. 2 is an absorbance spectrum of each of the solar cell of Example 1 and the solar cell comprising $N_3$ dye.
Figure 3:
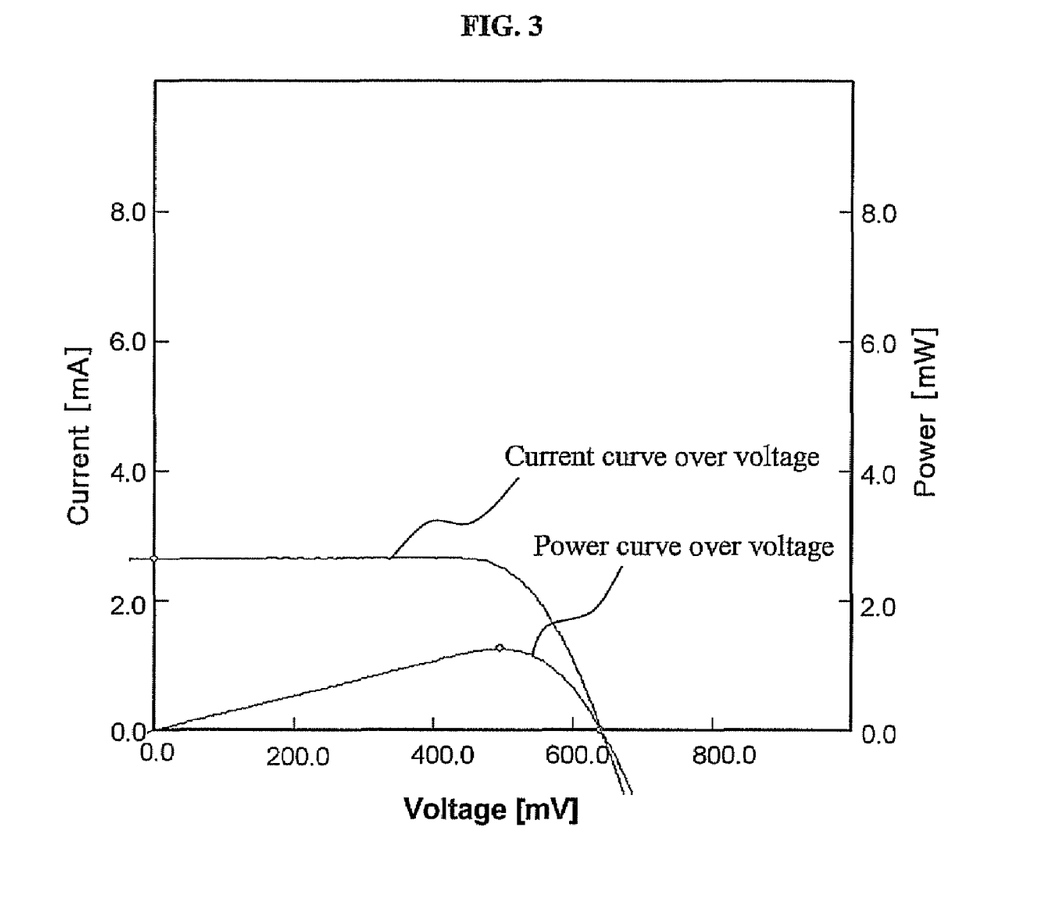
FIG. 3 is a graph showing current-voltage properties of the solar cell of Example 1.

In addition, as shown in FIG. 2, the solar cell comprising the dye of the present invention and the solar cell comprising the $N_3$ dye can be seen to have a very similar absorbance spectrum depending on the wavelength of light.

As described hereinbefore, the present invention provides a dye having a dispersant function and a solar cell comprising the same. According to the present invention, the dye has a dispersant functional group, it can simultaneously exhibit a dye function for absorbing light, because it is adsorbed on the surface of metal oxide particles, to thus produce excited electrons which are then transferred into the conduction band of metal oxide, and a dispersant function for preventing agglomeration of the particles to improve the uniformity of the metal oxide particles in the paste and film density. Therefore, the semiconductor electrode and solar cell manufactured using the dye of the present invention have greatly increased photoelectric efficiency and processibility.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A dye, which is represented by Formula 1 below:

Formula 1 wherein $R_a$, $R_b$, $R_c$ and $R_d$ are each independently $H^+$ or are represented by Formula 2 below, at least one of $R_a$, $R_b$, $R_c$ and $R_d$ being represented by Formula 2 below:

Formula 2 wherein $X_1$, $X_2$, $X_3$ and $X_4$ are each independently H or a methyl group, A is a substituted or unsubstituted $C_{6-30}$ arylene group, a substituted or unsubstituted $C_{6-30}$ arylalkylene group, or a substituted or unsubstituted $C_{6-30}$ cycloalkylene group, B is a substituted or unsubstituted $C_{1-20}$ alkyl group, a substituted or unsubstituted $C_{1-20}$ alkenyl group, or a substituted or unsubstituted $C_{1-20}$ alkynyl group, which may be present in a linear or branched type, m is an integer from 1 to 20, and n is 0 or 1.

2. The dye as set forth in claim 1, which is represented by any one of Formulas 3 to 6 below:

Formula 3

Formula 4

Formula 5

Formula 6 wherein X is $R_1$, $R_2$, $R_3$, $R_4$ and $R_5$ are each independently H or a methyl group, and m is an integer from 5 to 10, l is 0 or 1, and k is an integer from 2 to 10.

3. The dye as set forth in claim 2, which is represented by Formula 7 below:

Formula 7

4. A semiconductor electrode, comprising:
a transparent electrode, including a substrate and a conductive material applied thereon;
a metal oxide layer formed on the transparent electrode; and
the dye of claim 1, present in the metal oxide layer.

5. The semiconductor electrode as set forth in claim 4, wherein the substrate is a glass substrate, a plastic substrate, or a silica substrate.

6. A dye-sensitized solar cell, comprising:
the semiconductor electrode of claim 4;
an electrolyte layer; and
a counter electrode.

* * * * *